(12) United States Patent
Han et al.

(10) Patent No.: US 9,993,158 B2
(45) Date of Patent: Jun. 12, 2018

(54) APPARATUS FOR MEASURING CONDITION OF OBJECT

(71) Applicant: LG ELECTRONICS INC., Seoul (KR)

(72) Inventors: Sungho Han, Seoul (KR); Heesun Hong, Seoul (KR); Munseong Kang, Seoul (KR); Jaehoon Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 285 days.

(21) Appl. No.: 14/540,860

(22) Filed: Nov. 13, 2014

(65) Prior Publication Data

US 2015/0157208 A1    Jun. 11, 2015

Related U.S. Application Data

(60) Provisional application No. 61/913,918, filed on Dec. 10, 2013.

(30) Foreign Application Priority Data

Dec. 23, 2013    (KR) .................. 10-2013-0161866

(51) Int. Cl.
*A61B 5/00*    (2006.01)
*A61B 5/1455*   (2006.01)
(Continued)

(52) U.S. Cl.
CPC .......... *A61B 5/0064* (2013.01); *A61B 5/0073* (2013.01); *A61B 5/0075* (2013.01);
(Continued)

(58) Field of Classification Search
CPC .. A61B 5/0059; A61B 5/0064; A61B 5/14552
See application file for complete search history.

(56) References Cited

U.S. PATENT DOCUMENTS 6,293,940 B1    9/2001    Slatkine
6,413,267 B1    7/2002    Dumoulin-White et al.
(Continued)

FOREIGN PATENT DOCUMENTS

JP    3624925    3/2005
WO    2012082789    6/2012

OTHER PUBLICATIONS

PCT International Application No. PCT/KR2014/010850, Written Opinion of the International Searching Authority dated Feb. 12, 2015, 11 pages.
(Continued)

*Primary Examiner* — Michael Rozanski
(74) *Attorney, Agent, or Firm* — Lee, Hong, Degerman, Kang & Waimey

(57) ABSTRACT

The present disclosure provides a measurement apparatus including a light source configured to output light toward a first side of an object, a sensor positioned relative to the light source to permit the object to be positioned between the light source and the sensor, wherein the sensor is configured to sense the light transmitted through the object, and an optical transmitter disposed at an upper portion of the sensor and comprising a plurality of optical fibers configured to transfer the transmitted light to the sensor.

21 Claims, 11 Drawing Sheets

(51) Int. Cl.
A61B 5/107 (2006.01)
A61B 5/11 (2006.01)

(52) U.S. Cl.
CPC .......... *A61B 5/1079* (2013.01); *A61B 5/1122* (2013.01); *A61B 5/1128* (2013.01); *A61B 5/14552* (2013.01); *A61B 5/4528* (2013.01); *A61B 5/4842* (2013.01); *A61B 2562/146* (2013.01)

(56) References Cited

U.S. PATENT DOCUMENTS

| | | | |
|---|---|---|---|
| 2002/0190219 A1* | 12/2002 | Mooney | G01N 23/04 250/396 R |
| 2012/0071740 A1 | 3/2012 | Kaestle | |
| 2012/0283516 A1* | 11/2012 | Kang | A61B 1/07 600/182 |
| 2013/0059264 A1 | 3/2013 | Monty | |
| 2013/0289394 A1 | 10/2013 | Hielscher et al. | |

OTHER PUBLICATIONS

European Patent Office Application Serial No. 14869423.5, Search Report dated Sep. 11, 2017, 8 pages.

Netz, Uwe J. et al., "Optical tomography in the diagnosis of rheumatoid arthritis—method and implementation", Medical Laser Application, XP022114338, Jun. 2007, 8 pages.

* cited by examiner

APPARATUS FOR MEASURING CONDITION OF OBJECT

CROSS-REFERENCE TO RELATED APPLICATIONS

Pursuant to 35 U.S.C. § 119(a), this application claims the benefit of U.S. Provisional Patent Application Ser. No. 61/913,918, filed on Dec. 10, 2013, and the benefit of earlier filing date and right of priority to Korean Patent Application No. 10-2013-0161866, filed on Dec. 23, 2013, the contents of which are all incorporated by reference herein in their entireties.

BACKGROUND OF THE DISCLOSURE

1. Field of the Disclosure

This specification relates to an apparatus for measuring a condition of an object.

2. Background of the Disclosure

In general, X-ray, ultrasonic wave, computerized tomography (CT), and the like which are imaging diagnosis methods used in clinical medicine are methods of imaging anatomical changes due to diseases. Biochemical and molecular changes precede anatomical changes upon an occurrence of a disease. Hence, recently, a diagnostic paradigm is changing into molecular imaging for diagnosing diseases at incipient stages through imaging.

Molecular imaging is a technology of imaging physiological changes, for example, a method of diagnosing a lesion by evaluating various changes at a molecular level within cells through imaging. The molecular imaging may allow for diagnosing physiological changes in disease progression through imaging, to prevent and control the disease prior to treatment of the lesion.

However, current devices for diagnosing via molecular imaging require extremely large and high-priced systems such as positron emission tomography (PET). This causes limitations on commercialization and use of such devices. Therefore, a measurement apparatus, which is implemented into a smaller and accessible form of various platforms which is capable of carrying out a molecular imaging diagnosis may be considered.

SUMMARY OF THE DISCLOSURE

Therefore, an aspect of the detailed description is to provide a measurement apparatus for molecular imaging diagnosis capable of being commercialized into a small system.

Another aspect of the detailed description is to provide a measurement apparatus capable of easily measuring conditions of an object using transmitted light.

To achieve these and other advantages and in accordance with the purpose of this specification, as embodied and broadly described herein, there is provided a measurement apparatus according to one exemplary embodiment, including a light source unit configured to output light toward a first side of the object, a sensor unit configured to sense the light transmitted through the object and received on a second side of the object opposite the first side, and an optical fiber unit disposed at an upper portion of the sensor unit and comprising a plurality of optical fibers configured to transfer the transmitted light to the sensor unit.

In accordance with one exemplary embodiment disclosed herein, the optical fiber unit may include a top side configured to provide a surface on which the object is located, and a bottom side adjacent to the sensor unit.

In accordance with another exemplary embodiment disclosed herein, the the sensor unit may be configured to convert the transmitted light to image data corresponding to an image.

In accordance with another exemplary embodiment disclosed herein, apparatus may further include a controller configured to receive the image data and determine a condition of the object by comparing the received image data to stored image data.

The light source unit may be movable to vary an output position of the light such that a measuring point of the object is changed. The light source unit may include a laser diode configured to output a near-infrared laser beam, and a mirror configured to reflect the near-infrared laser beam to be directed toward the sensor unit. The mirror may be tilted to change an angle of a reflective side of the mirror, or moved along a path to change a position of the mirror.

The laser diode may be movable to change an output position of the near-infrared laser beam.

The light source unit may include an optical direction unit disposed between the mirror and the optical fiber unit and configured to direct the near-infrared laser beam reflected from the mirror toward the object in a direction perpendicular to a surface of the optical fiber unit.

The sensor unit may be spaced apart from the light source unit to define a gap between the optical fiber unit and the light source to receive the object.

The light source unit may include a plurality of light sources each separately controllable to output light.

In accordance with another exemplary embodiment disclosed herein, the measurement apparatus may include an object information sensor configured to detect geometric information related to the object. The object information sensor may be configured to detect the geometric information using light output from the light source unit and reflected from the object. The information sensor unit may include an object detection unit configured to measure at least a surface height or a shape of the object at a measurement position of the object, and the object detect unit may include a position displacement sensor or a 3D scanning sensor In accordance with another exemplary embodiment disclosed herein, the light source unit may be configured to output light of a predetermined intensity and wavelength.

The present disclosure may also provide a measurement apparatus, including a light source unit configured to output light toward an object, an object information sensor configured to detect geometric information related to the object, a sensor unit configured to form a transmission image from the light output by the light source unit and transmitted through the object, and a light transfer unit that is disposed between a top surface of the sensor unit and the object and configured to transfer the transmitted light to the sensor unit.

In accordance with various embodiments of the measurement apparatus of the present disclosure, an apparatus of imaging physiological changes can be commercialized. This may allow for easily diagnosing conditions or encouraging preventative attention to health by observing physiological changes of a human body through preliminary management at home or in communities. In more detail, customized diagnosis, such as a diagnosis in terms of prevention and management, an observation of effectiveness of treatments, and biophotonics can be made available to a wide range of users. Also, since the measurement apparatus can image physiological changes for a part of an object, including non-human anatomy, physiological changes of plants or foods may also be measured.

Also, with the use of a low-priced laser diode and an optical fiber-based optical system, a measurement apparatus which is low-priced, portable, open-source, having high accuracy can be easily made available and implemented. This may allow the measurement apparatus for diagnosing based on molecular imaging to be implemented and made widely available.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The accompanying drawings, which are included to provide a further understanding of the disclosure and are incorporated in and constitute a part of this specification, illustrate exemplary embodiments and together with the description serve to explain the principles of the disclosure.

In the drawings.

DETAILED DESCRIPTION OF THE DISCLOSURE

Description will now be given in detail of a measurement apparatus according to the exemplary embodiments, with reference to the accompanying drawings. For the sake of brief description with reference to the drawings, the same or equivalent components will be provided with the same reference numbers, and description thereof will not be repeated.

Figure 1:
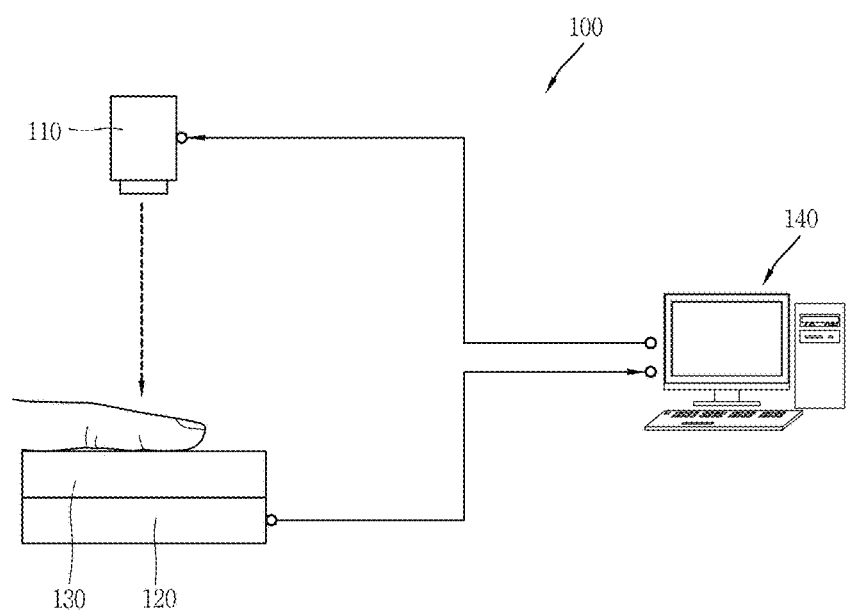
FIG. 1 is an illustration of a configuration related to a measuring method in accordance with one exemplary embodiment disclosed herein.

FIG. 1 is a conceptual view of a measuring method in accordance with one exemplary embodiment disclosed herein.

As illustrated in FIG. 1, an object 102 is placed on a specific position of a measurement apparatus 100. The object 102 may be a portion of a human body (a finger in this exemplary embodiment). Here, the present disclosure may not be limited to this. The object may also be another portion of the human body, for example, a wrist, an elbow, a shoulder, a foot, an ankle, a knee and the like.

A measurement apparatus 100 may output light of a specific wavelength band (electromagnetic wave of a specific wavelength band) toward the object 102, and sense light transmitted through the object (hereinafter, referred to as "transmitted light"). The output light of the specific wavelength band may be near infrared having wavelengths in the range of 650 nm to 1000 nm. However, the present disclosure may not be limited to this, and the light may belong to another wavelength band. The near infrared light may be attenuated when transmitted through a portion of the human body, and the measurement apparatus 100 may measure a lesion using the light attenuation.

The measurement apparatus 100 may include a light source unit 110, a sensor unit 120, and an optical fiber unit 130.

The light source unit 110 may be configured to output the light of a specific wavelength band and controlled by a controller 140. The sensor unit 120 may sense the transmitted light to provide information related to the transmitted light to controller 140, and the controller 140 may compare the transmitted light with preset data so as to measure various conditions of the object. For example, if the location of the output light on the object is adjacent to a joint of a finger, a first part of the output light may be reflected, a second part may be absorbed, and a third part may be transmitted therethrough. In this example, physiological changes or conditions of the joint may be detected using the information related to the transmitted light, and various conditions including for example an advanced degree of a lesion present at the joint (for example, resulting from arthritis) may be measured accordingly.

According to the measuring method, a customized diagnosis including prevention and management, a continuous observation of treatment effects, and biophotonics, may be implemented. Hereinafter, the measuring method will be described in more detail, and a detailed structure of a measurement apparatus as well as a measuring method will be described.

Figure 2:
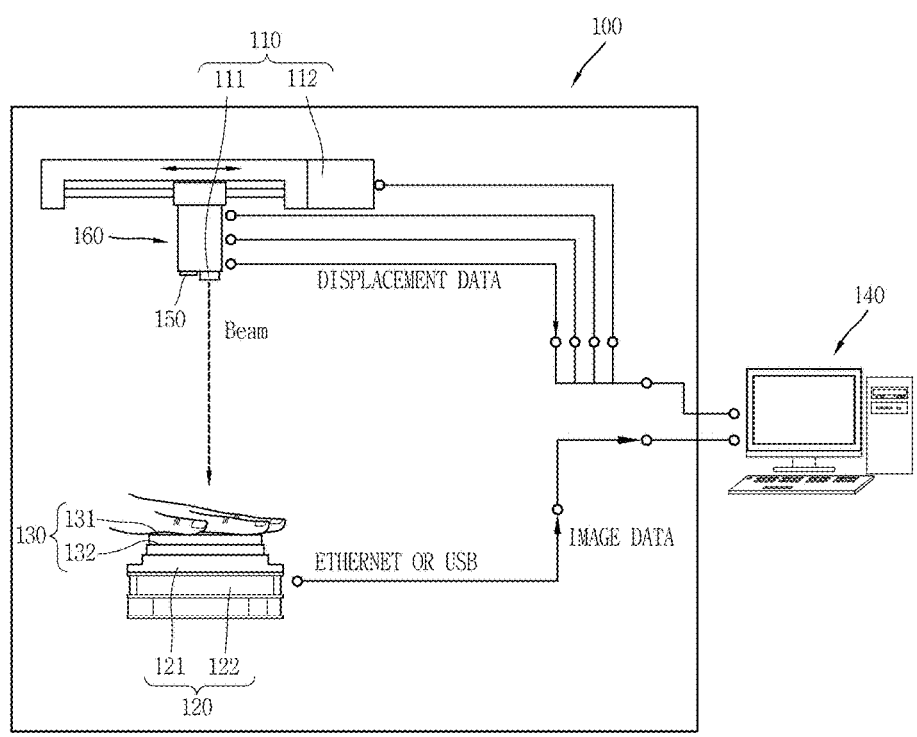
FIG. 2 is an illustration of one exemplary embodiment of a measurement apparatus disclosed herein.
Figure 3:
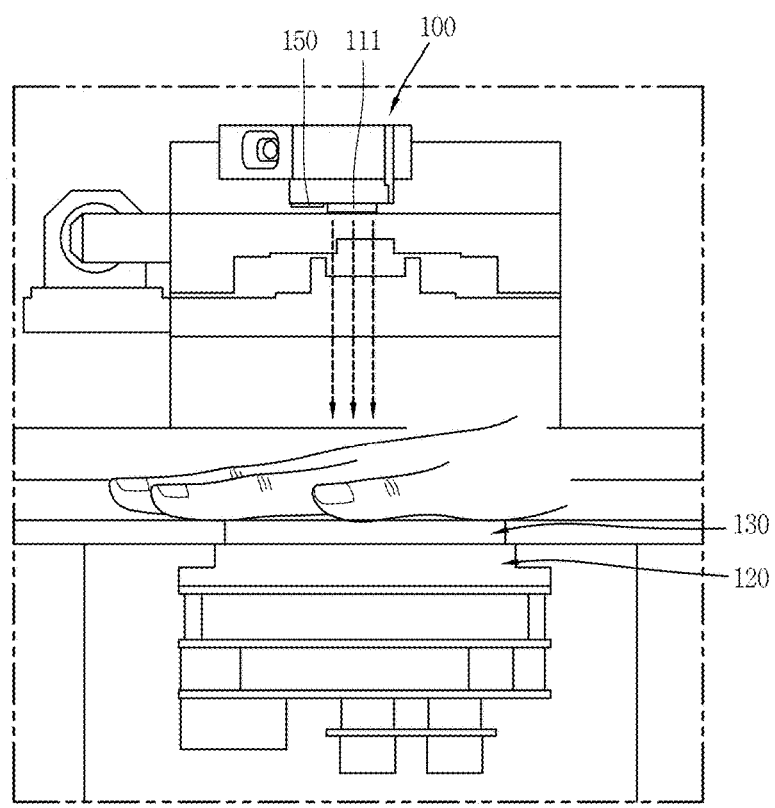
FIG. 3 is an alternate view of the measurement apparatus of FIG. 2.
Figure 4:
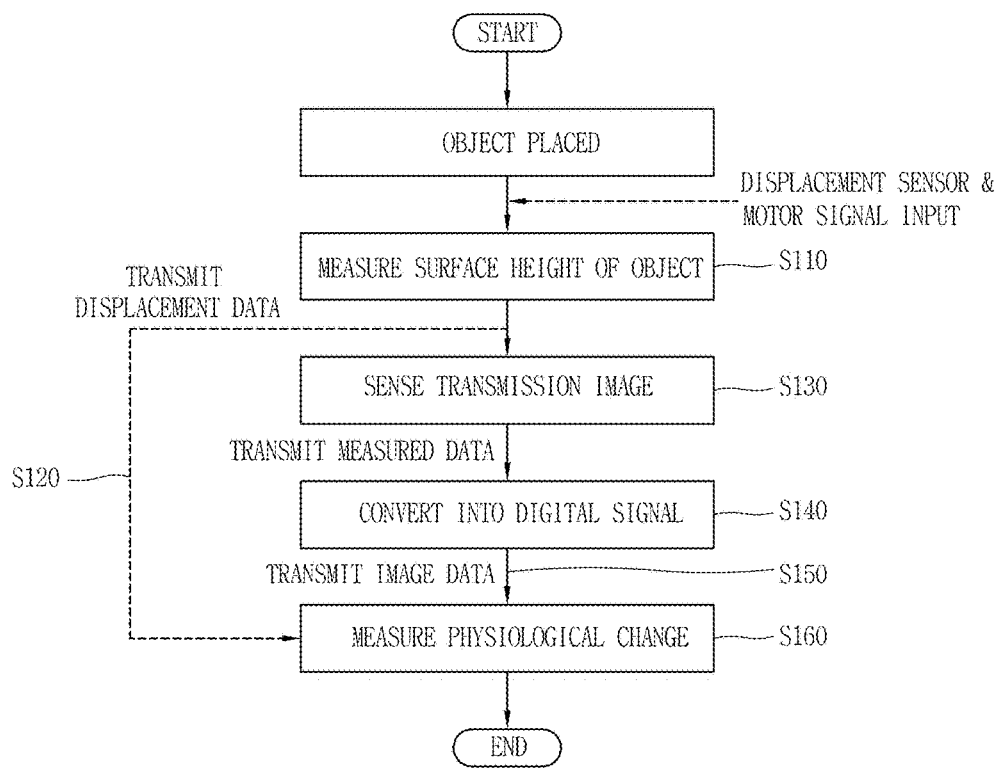
FIG. 4 is a flowchart illustrating an exemplary measurement using the measurement apparatus of FIG. 2.
Figure 5:
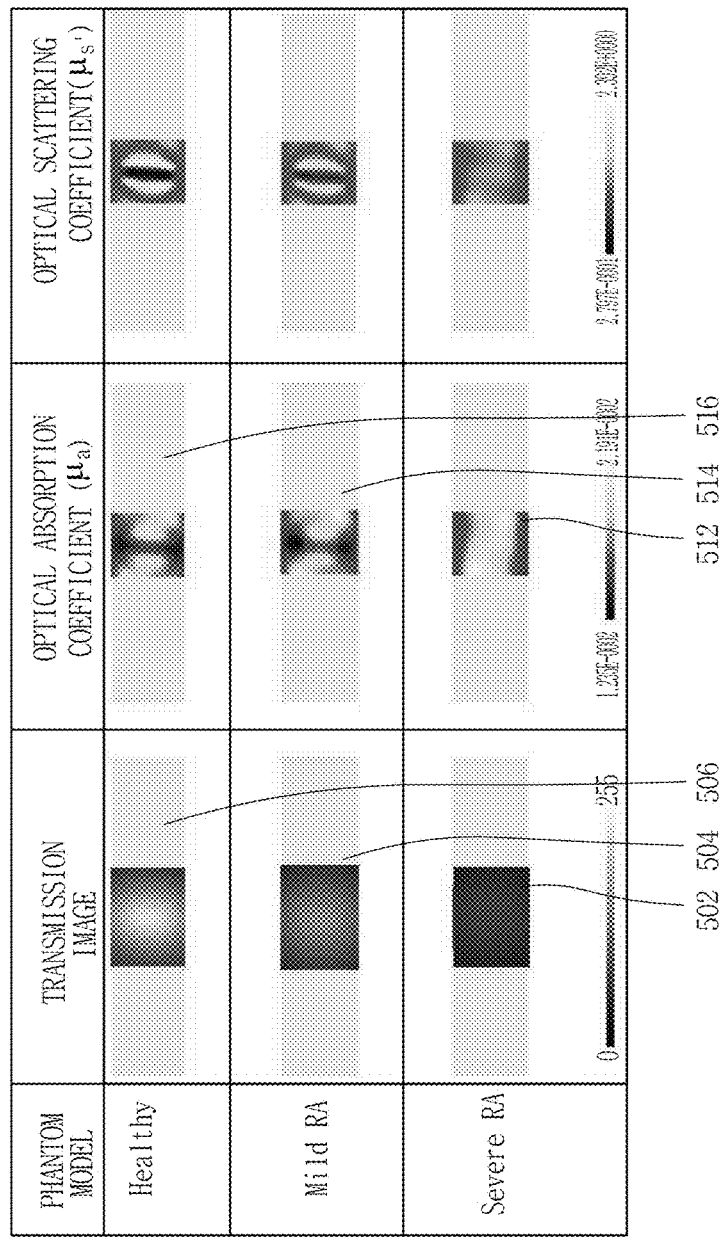
FIG. 5 is a view illustrating examples of measurement results obtained by an embodiment of a measurement apparatus disclosed herein.

FIG. 2 is a conceptual view illustrating one exemplary embodiment of a measurement apparatus disclosed herein, FIG. 3 is an alternate view of the measurement apparatus of FIG. 2, FIG. 4 is a flowchart illustrating an exemplary measurement using the measurement apparatus of FIG. 2, and FIG. 5 is a view illustrating example measurement results obtained by a measurement apparatus disclosed herein.

With reference to FIG. 2, a light source unit 110 of the measurement apparatus 100 may output light towards an object. For example, the light source unit 110 may be provided with a laser diode 111 which outputs near infrared laser beams.

The laser diode 111 may be a semiconductor device emitting light, which is viewed when a current flows therethrough or belongs to the same frequency and phase in an infrared (IR) spectrum. The laser diode 111 may output light of uniform intensity at a preset wavelength band. However, the present disclosure may not be limited to this. The light source unit 110 may also output light with modulated intensity. For example, the light source unit 110 may output light which has a wavelength and a phase of a sine wave, and the sensor unit 120 may sense the changes of the wavelength and the phase to measure the condition of the object.

Also, a light source of the light source unit 110 disclosed herein may not be limited to the laser diode. For example, a light-emitting diode (LED) and the like may be employed as the light source. That is, the light source unit 110 may be configured to output broadband light. In another example, the light source of the light source unit 110 disclosed herein may be a pulse laser diode which outputs pulse laser beams.

As illustrated in FIG. 2, the laser diode 111 may be connected to a motor 112 wherein the laser diode is moved in response to driving of the motor 112. In a more detailed example, a displacement sensor 160 may be connected to the motor 112, which will be discussed later in greater detail. The light source unit 110 may be allowed to move (change) an output position of the light on the object such that a measuring point of the object can be changed while the object is secured.

In some embodiments, laser diode 111 may be slidable along a path and configured to output light at each of a plurality of points along the path. That is, the laser diode 111 may output light at one point and move to another point within the path. A selection of the output point may be controlled by a controller 140. In more detail, the controller 140 may control the motor according to control information based on receiving a user selection with respect to the output points.

However, the present disclosure may not be limited to this. For example, the light source unit 110 may be moved while outputting the light generated by the laser diode 111 according to control information regarding the desired scan. In more detail, in order to transmit the laser beams across a specific region of the object or along a specific plane of the object, the light source unit 110 may output the light, such as laser beams, in a raster-scan manner. The output method may be related to a single point light output, however the present disclosure may not be limited to this. Embodiments configured to allow line scanning with respect to a planar light output are also considered.

With reference to FIG. 3 as well as continued reference to FIG. 2, the sensor unit 120 of the measurement apparatus 100 may sense the transmitted light, which has been transmitted through the object, for measuring a condition of the object. As illustrated in the drawings, the sensor unit 120 may be spaced apart from the light source unit 110 to form a spacing such that the object can be secured within the spacing.

The sensor unit 120 may include a charge-coupled device (CCD) camera 121 and a circuit board 122.

The CCD camera 121 may be mounted onto the circuit board 122 and configured to capture an image of the transmitted light. The circuit board 122 may be an analog front end (AFE) board, configured to convert an analog signal of the captured image into a digital signal. However, the present disclosure may not be limited to this. For example in other embodiments, an array type photo detector may replace the CCD camera to capture the image. The array type photo detector may include a photo diode (PD), an avalanche photo diode (APD), a single photo avalanche diode (SPAD), or the like, which include a plurality of point detectors arranged thereon.

The optical fiber unit 130 of the measurement apparatus 100 may include a plurality of optical fibers (not illustrated), which are disposed to cover the sensor unit 120, such that the transmitted light, transmitted and sensed through the object, can be received at the sensor unit 120 without a distributional change. The plurality of optical fibers may form one bundle, so as to transmit the light transmission image to the sensor unit 120.

The position of the laser beam output from the laser diode may be adjacent to a specific point of a top surface of the object, but scattered within the object so as to be widely distributed when received or sensed on the other side of the object (a bottom opposite to the top surface). The distribution of the light on the bottom surface may form the transmission image captured by the sensor unit 120. Therefore, the optical fiber unit 130 may be referred to as a light transfer unit, which is disposed between a surface of the sensor 120 and the object and configured to transfer the light sensed at the bottom surface of the object to the sensor unit. To this end, the plurality of optical fibers may be arranged in a manner of dividing the transmission image into a plurality of portions for transfer.

In more detail, the optical fiber unit 130 may include an upper portion 131 and a lower portion 132. The upper portion 131 may correspond to a portion of the light source unit 130, which is directly opposite to and faces the light source unit 110. Also, the upper portion 131 may be formed such that the object can be located, secured to, or placed thereon. For example, the upper portion 131 may be formed on a plane so as to be contactable directly with the object. As a more detailed example, the plurality of optical fibers may be arranged such that the collective surface of the plurality of optical fibers which are disposed in parallel to form the upper surface 131.

In some embodiments, the optical fiber unit 130 may be a fiber optic face plate (FOFP). In this case, an upper surface of the FOFP may be formed such that the object can be closely adhered thereto. The FOFP may be an optical fiber which collects the light which has been transmitted through a portion of the object, and transfers the collected transmitted light to the CCD camera 121. The FOFP may serve to prevent an introduction of external light to the image capturing system.

As illustrated in the drawings, the lower portion 132 may be disposed adjacent to the sensor unit 120. For example, the lower portion 132 may be formed by arranging exit surfaces of the plurality of optical fibers, and be bonded to the upper surface of the sensor unit 120. As another example, the lower portion 132 may be spaced apart from the upper surface of the sensor unit 120 by about 100 to 500 µm. In this case, the optical fiber unit 130 and the sensor unit 120 may be mounted onto separate structures, respectively.

Upon receiving the transmission image from the optical fiber unit 130, the sensor unit 120 may change the transmission image into a digital signal. The controller 140 may measure the condition of the object by comparing the transmission image with preset data using the digital signal. For example, the controller 140 may measure the condition of the object by measuring an attenuated degree of the intensity of the transmitted light. In this case, the optical fiber unit 130 may allow transmission of the transmitted light directly to the sensor unit without a change in intensity of the transmitted light, and the sensor unit may be a sensor for measuring the intensity of the transmitted light.

The controller 140 may output a graphic user interface (GUI) via a display for interaction with a user. Among other functions, the controller 140 may also control, for example, signal processing, operation of algorithms, and execution of functions of the circuit board of the sensor unit (for example, the conversion of the image signal into a digital signal).

In some embodiments, the controller 140 may measure geometric information related to the object in addition to data for measuring the condition of the object. To this end, the measurement apparatus 100 may further include an information sensor unit 150 that is configured to sense the geometric information related to the object.

The information sensor unit 150 may be arranged to sense the light output from the light source unit 110 which is reflected off of a surface of the object. In more detail, the information sensor unit 150 may be included in a displacement sensor 160, which measures a surface height of the object at a portion of the object to which the light output from the light source unit 110 is directed. The information sensor unit 150 may also measure a 3D shape of the object.

In general, a displacement sensor is provided with a laser diode and a reflected light sensor. The reflected light sensor may sense the reflected light, such that the geometric information related to the object can be measured. In this case, a position or a surface height of a point from which the light of reflected may be detected by triangulation. In more detail, light of the laser is transmitted or irradiated onto a particular point of the object, and light which is scattered on the surface is partially converged such that information of the scattered light is received by a position detector. Thus a displacement of the object can be decided. In addition to displacement sensors utilizing laser diodes, other displacement sensor configurations are also considered and may be implemented in various embodiments.

In the exemplary embodiment, the displacement sensor 160 may sense the reflected light from the object. In this case, the laser diode of the light source unit 110 may serve as the laser diode of the displacement sensor 160. That is, the displacement sensor 160 may share the laser diode of the light source unit 110. Therefore, the information sensor unit 150 may utilize information received by the sensor which senses the reflected light.

From a different perspective, the displacement sensor 160 may be configured to include the light source unit as well as the information sensor unit. In this case, the light source unit and the information sensor unit 150 may be integrally formed with each other to be moved together in response to movement of the displacement sensor 160. Therefore, the motor 112 may be connected to the displacement sensor 160 so as to control the movement of the information sensor unit 150.

The foregoing description has been given of the structural perspective. Hereinafter, the measuring method will be described in more detail.

Referring to FIG. 4, when an object is placed in a measuring position, a surface height of the object may be measured (S110). Here, a displacement sensor may be turned on, utilizing a light source such as a near infrared laser beam of 650 to 1000 nm. An information sensor unit of a displacement sensor may sense light of the laser beam reflected from the object and measure geometric information related to the object. The geometric information, for example, may include a surface height, positional displacement, or a 3D image of the object. In this case, the measured data may be transmitted to a controller (for example, a data processor or an external PC) (S120).

Next, a sensor unit positioned at a side of the object opposite the light source may sense a transmission image (S130) which includes data detected via light transmitted through the object. The sensor unit may convert the transmission image into a digital signal (S140). In this case, the converted digital signal may be transmitted as image data to the controller (for example, a data processor or an external PC) (S150).

Here, the surface height measurement (S110) and the sensing of the transmission image (S130) may be carried out simultaneously or in consecutive order.

In order to detect transmission images and positional displacements from a plurality of portions of the object, the displacement sensor may be moved with respect to the object to positions corresponding to the specific portions. In this case, the displacement sensor may be moved by driving a motor configured to move the sensor in a desired path.

Finally, the controller may measure data of the object including a physiological change of a specific portion of the object (S160) using the information measured by the displacement sensor (S120) and the image data measured by the sensor unit (S150).

As aforementioned, this exemplary embodiment utilizes the displacement sensor as the light source and accordingly may allow implementation of a low-priced, reduced-size measurement apparatus.

FIG. 5 shows example images which may be obtained using the measurement apparatus of an embodiment. Referring to FIG. 5, three objects which exhibit observable measured differences are imaged using the measurement apparatus of this embodiment. Using such example images, the condition of the object may be observed, including conditions related to mild arthritis and severe arthritis which may result in images that are observably distinctive from one another.

For example, it can be noticed that a darker transmission image (502) is obtained from a sample exhibiting severe arthritis as opposed to a transmission image (504) obtained from a sample exhibiting mild arthritis, which is observably darker still than a transmission image (506) obtained from a healthy sample exhibiting no arthritis.

Further, an image with an optical absorption coefficient ($\mu a$) and an image with an optical scattering coefficient ($\mu s'$) for each of the healthy (516), mild arthritis (514), and severe arthritis (516) samples, may be observably different. In such a manner, an analysis of tomographic images of the three examples exhibiting different degrees of arthritis using an embodiment of the measurement apparatus according to the present disclosure may enable a quantitative diagnosis of rheumatoid arthritis, or other conditions which may result in observable differences in the images.

Additionally, measurement results related to light absorption, fluorescence, and oxygen saturation may also be utilized in various diagnoses. For example, in the absorption and fluorescence tests, when optical absorption is increased in response to an increase of synovial fluid, a fluorescent material is locked in an inflammatory capillary structure. As a result, different absorption and fluorescence levels are observable. Also, in a tissue oxygen saturation test, an increase in oxygen saturation (StO2) may be observed.

Therefore, the measurement results by the measurement apparatus disclosed herein can be used as indexes of diagnosing early stage arthritis. However, the present disclosure may not be limited to this, and the measurement apparatus disclosed herein may also be applied as an apparatus of measuring various other levels and conditions, such as tissue optical index (TOI), bound water index (BWI), and the like.

Figure 6A:
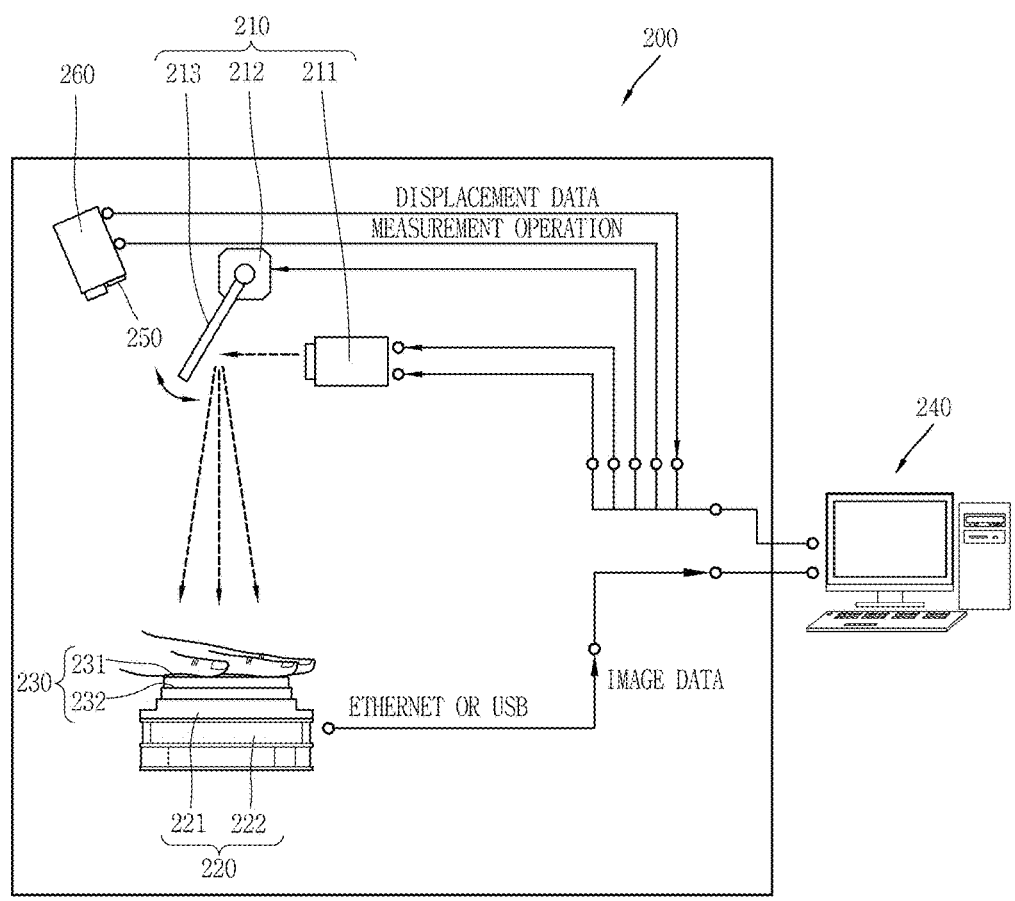
FIGS. 6A and 6B are illustrations of exemplary embodiments of a measurement apparatus disclosed herein.
Figure 6B:
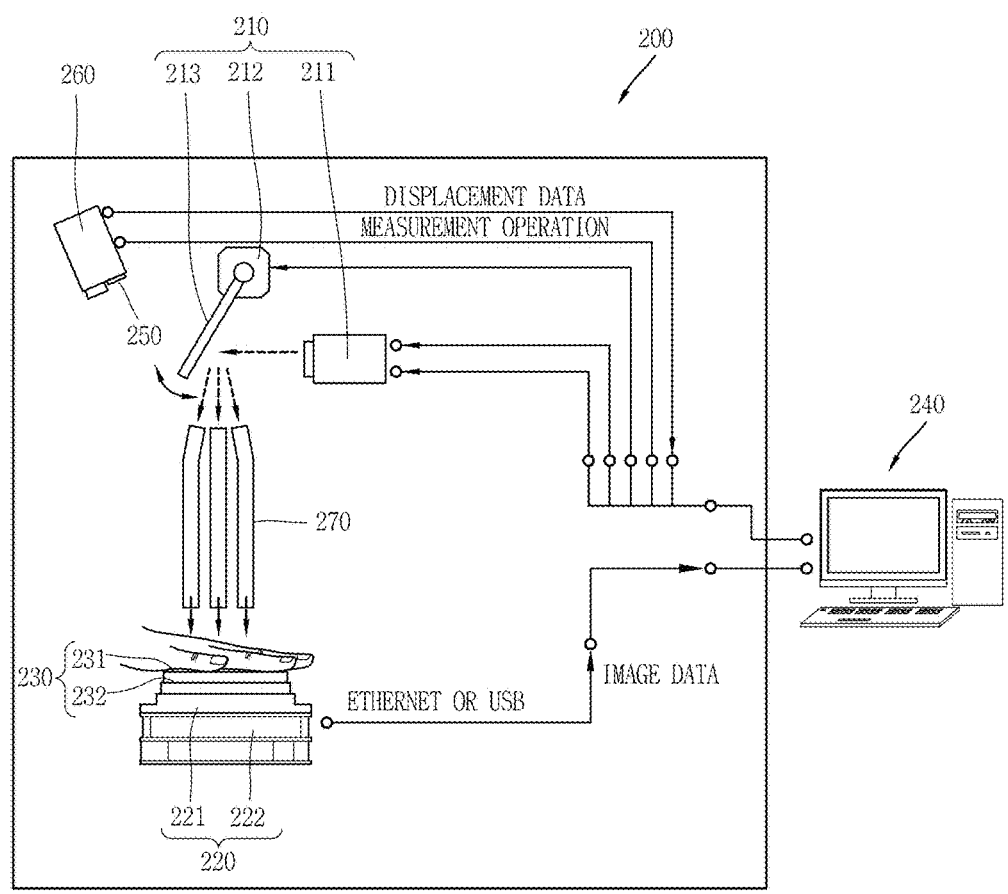
Figure 7:
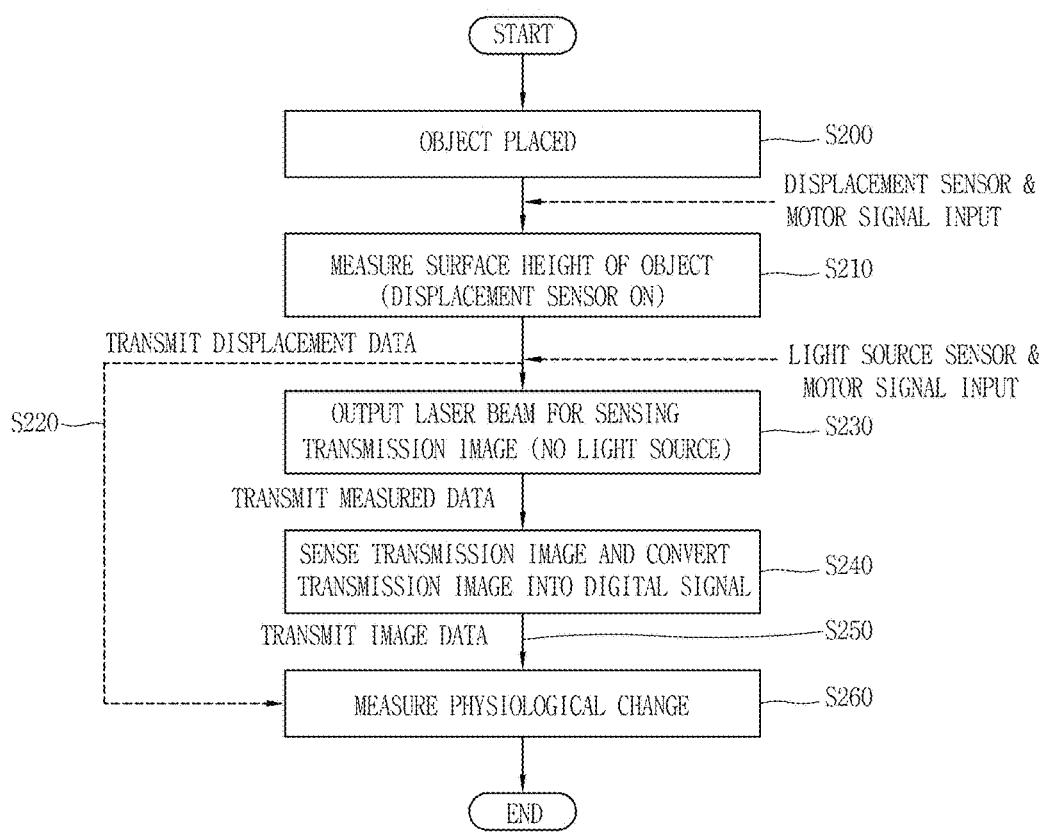
FIG. 7 is a flowchart illustrating an exemplary measurement using the measurement apparatus of FIG. 6.

Hereinafter, another exemplary embodiment will be described. FIGS. 6A and 6B are conceptual views illustrating another exemplary embodiment of a measurement apparatus disclosed herein, and FIG. 7 is a flowchart illustrating an exemplary measurement using the measurement apparatus of FIGS. 6A and 6B.

As illustrated in FIGS. 6A and 6B, a measurement apparatus 200 may include a displacement sensor 260 and a light source unit 210, which are separate from each other.

The light source unit 210 may be configured to output light of a specific wavelength band, wherein the light source unit is controlled by a controller 240. The light source unit 210 may be configured such that at least a part thereof can be moved to vary an output position of the light. Alternatively, an information sensor unit 250 may be located at a fixed position. The information sensor unit 250 may be included in a displacement sensor 260, which measures a surface height of an object at a portion of the object onto which the light from the light source unit 210 is directed, and in this case, the displacement sensor 260 may be fixed.

In more detail, the light source unit 210 may include a laser diode 211, and a mirror 213. The laser diode 211 may be configured to output near infrared laser beams. The mirror 213 may reflect the laser output from the laser diode 211 and direct the reflected laser toward the sensor unit.

Referring to FIG. 6A, an angle of the mirror 213 may be variable to change the direction output of the reflected light. To this end, a motor 212 may be operably connected to the mirror 213, and controlled by the controller 240. However, the present disclosure may not be limited to this. For example, in an embodiment without a mirror 213, the laser diode 211 itself may be configured to be tilted in various angles. In this case, the direction of the output laser may also be varied.

In another embodiment shown in FIG. 6B, an optical direction unit 270 may be disposed between the mirror 213 and an optical fiber unit 230, such that light reflected from the mirror 213 can be perpendicularly directed onto the object, irrespective of an angle of the mirror 213.

The optical direction unit 270 may be configured such that light reflected off the mirror 213 scattered in a direction not directly leading to the object may be directed by the optical direction unit 270 to be emitted directly perpendicular to a surface of the object. For example, the optical direction unit 270 may be implemented as one or more optical fibers, which includes a portion positioned at an angle to align with the reflected light and another portion which extends in a direction perpendicular to the object in order to direct the light.

The optical fiber unit 230 of the measurement apparatus 200 may be configured to reduce a distribution of the light transmitted through the object by a predetermined ratio and to transfer the transmitted light toward the sensor unit 220. To this end, the optical fiber unit 230 may be a fiber optic taper (FOT) with a reduced section, for example. In this case, the optical fiber unit 230 may divide a transmission image formed by the transmitted light into a plurality of portions, reduce each divided portion, and transfer the transmission image to the sensor unit 220. For example, the FOT may be formed so that an area of an upper portion is 5×5 and an area of a lower portion is 1×1.

However, the present disclosure may not be limited to this. For example, similar to the embodiment described with reference to FIGS. 2 and 3, the optical fiber unit 230 may be configured such that the area is not reduced along its length. Accordingly, the optical fiber unit 230 may transfer the transmission image formed by the transmitted light without the distributional change.

FIG. 7 shows a flowchart according to another embodiment of the present disclosure. First, when an object is placed on a measuring position (S200), a surface height (and/or a 3D shape) of the object may be measured (S210). In this case, the displacement sensor 260 may be turned on such that light is output toward the object. At this time, the information sensor unit 250 of the displacement sensor 260 may sense light reflected from the object to measure geometric information related to the object. The displacement sensor 260 may be provided with a laser diode or a light-emitting diode for outputting the light. In this case, measured displacement data may be transmitted to a controller (for example, a data processor or an external PC) (S220).

Next, the light source unit may be turned on to output a laser beam (S230). The sensor unit may sense a transmission image formed by the light transmitted through the object, and convert the transmission image into a digital signal (S240). Here, the surface height measurement (210) and the sensing of the transmission image may be carried out simultaneously or in consecutive order. In this case, the converted digital signal may be transmitted as image data to a controller (for example, a data processor or an external PC) (S250).

Here, in order to detect transmission images and displacements from a plurality of specific portions of the object, at least part of the light source unit may be movable to various positions. Accordingly, a point of the object at which the laser light is directed may be varied.

Finally, the controller may measure various object data including physiological changes using the displacement measured by the displacement sensor and the image data measured by the sensor unit (S260).

According to the aforementioned measurement apparatus, a range of light output from the light source unit may be widened and controlled more accurately. Other embodiments may include configurations allowing the variation of the information sensor unit and a position of light. Hereinafter, examples of such embodiments will be described.

Figure 8A:
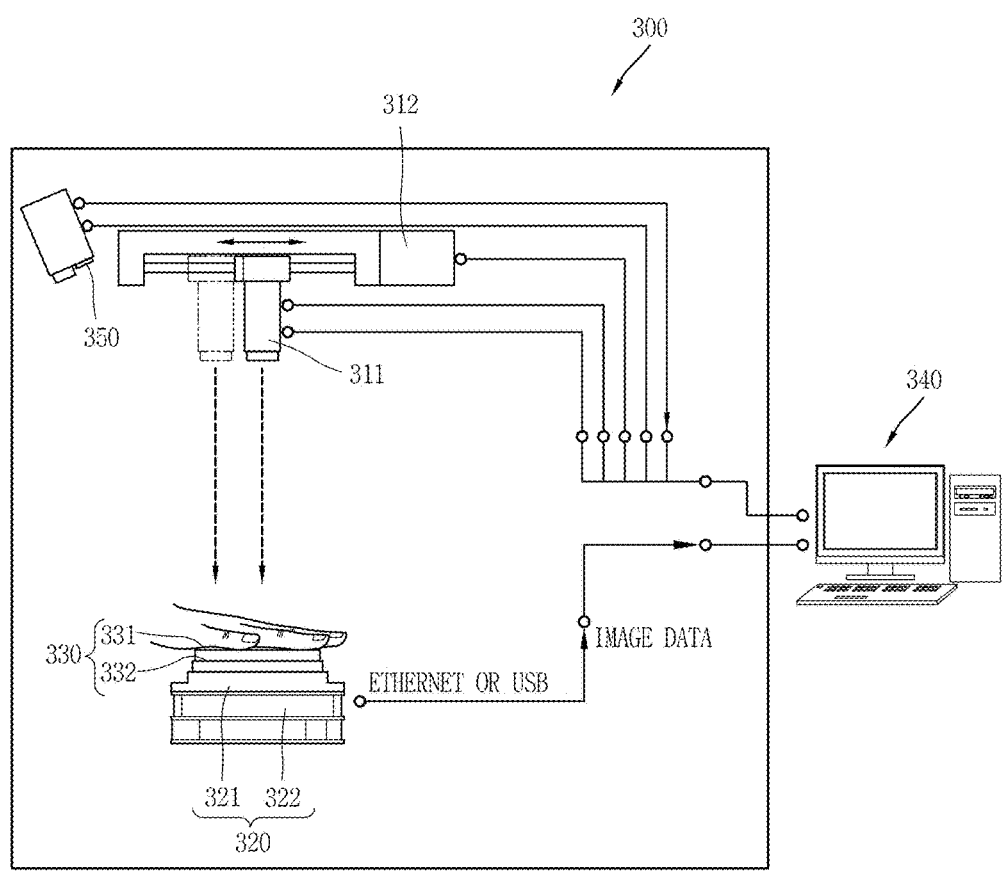
FIGS. 8A to 8C are illustrations of other exemplary embodiments of a measurement apparatus disclosed herein.
Figure 8B:
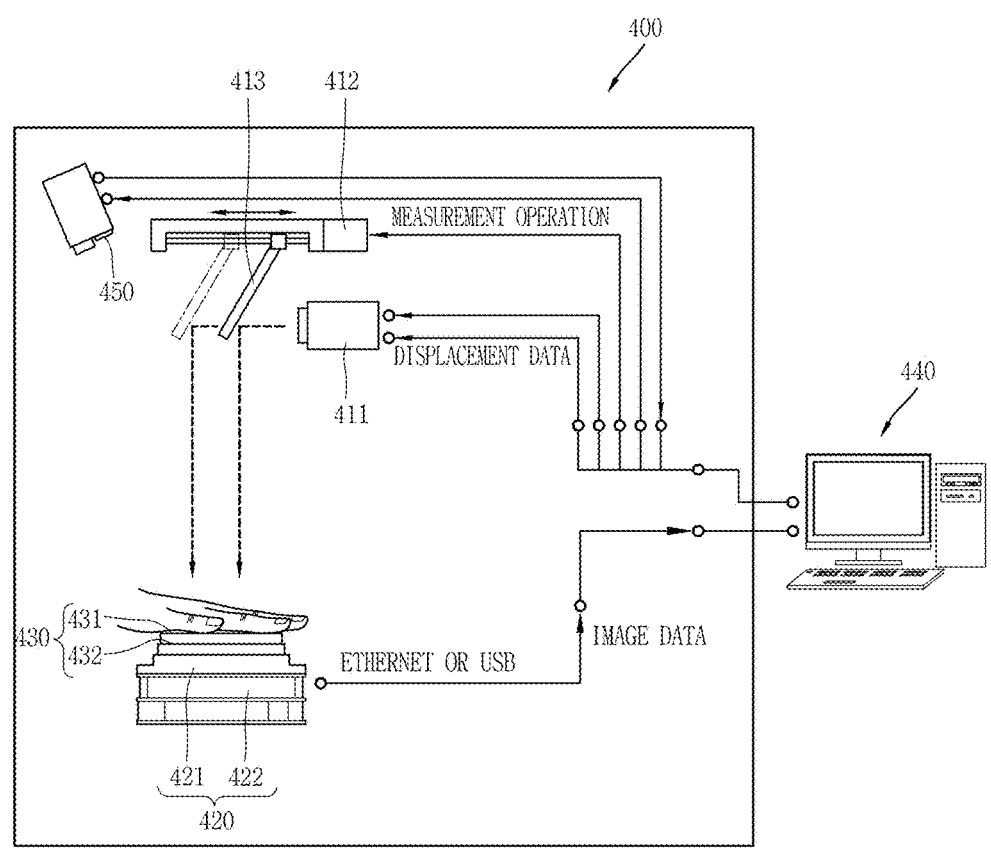
Figure 8C:
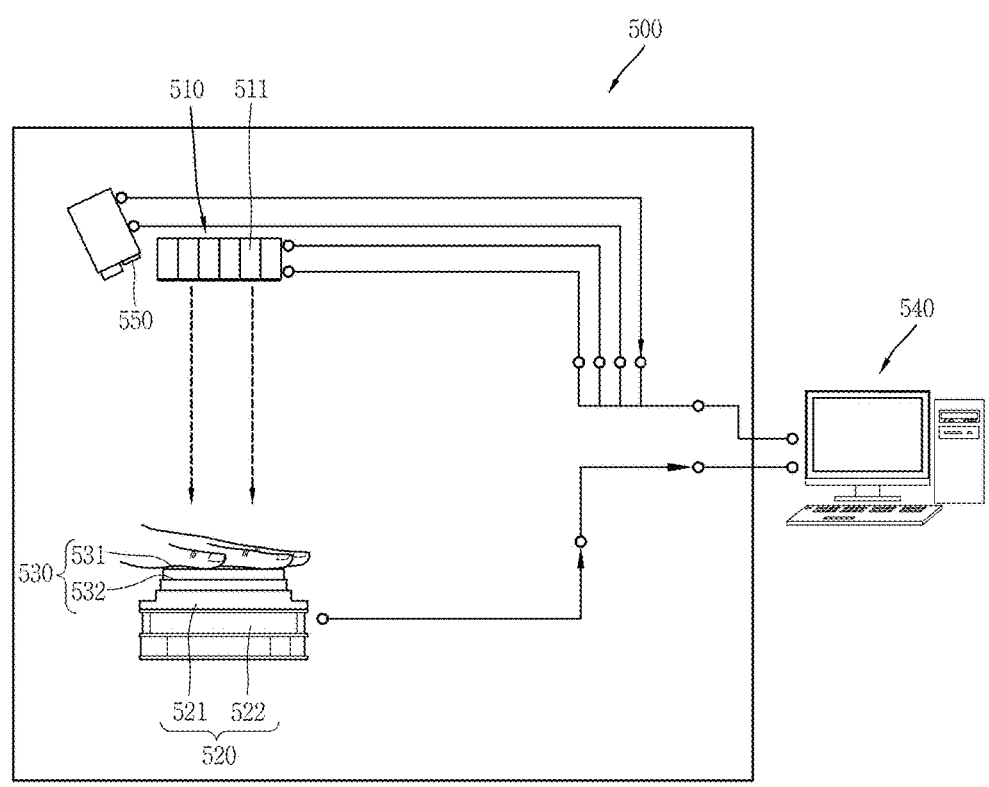

FIGS. 8A to 8C are conceptual views illustrating exemplary embodiments of the measurement apparatus of FIG. 6.

Referring to FIG. 8A, an information sensor unit 350 may be fixed in position. Instead a laser diode 311 may be slidable to change a position of the output point of light. To this end, the laser diode 311 may be positioned such that an output portion thereof faces a sensor unit 320. A mirror may or may not be disposed between the laser diode 311 and the sensor unit 320.

The laser diode 311 may also be connected to a motor 312. In response to driving of the motor 312, the laser diode 311 may be moved in a desired direction. In some embodiments, the path of movement of the laser diode is parallel to a surface of the sensor unit 320. In other embodiments, the laser diode may be secured at any point along the sliding path in order to consistently output laser towards the object.

In another embodiment shown in FIG. 8B, an information sensor unit 450 and a laser diode 411 may be fixed in position. Instead, a mirror 413 may be provided and the mirror may be slidable to vary the resulting output location of light. The laser diode 411 may output light toward mirror 413, and the mirror 413 may be controlled to be moved along a path parallel to a surface of sensor unit 420. The mirror 413 may be secured at any point along the path in order to consistently direct light output from laser diode 411. For the purpose, the mirror 413 may be connected to a motor 412 to enable the movement.

As another embodiment, referring to FIG. 8C, a light source unit 510 may be provided with a plurality of light sources. For example, the light source unit 510 may include a plurality of light sources arranged to form an array, and the plurality of light sources may be controlled such that a controlled number of the light sources can output light. The plurality of light sources may be light sources at a plurality of wavelengths.

In an embodiment, several light sources of the plurality of light sources, corresponding to desired measuring positions may be controlled to output light in a sequential manner. Accordingly, the changes of measuring positions on the object can be allowed even in a state where the light source unit 510 and the information sensor unit 550 are fixed.

Also, at least one pair of the plurality of light sources may be controlled to output light simultaneously. For example, in the measurement of oxygen saturation, a plurality of light sources for oxyhemoglobine and dioxyhemoglobin are required. Therefore, since the measurement apparatus according to this embodiment is configured such that the plurality of light sources can be individually controlled, the measurement apparatus can carry out the oxygen saturation measurement by controlling the required number and type of light sources. Here, the aforementioned measurement apparatus may not be limited to the structure in which the light source unit includes only a single laser diode, but it may include embodiments in which the light source unit includes a plurality of laser diodes. Also, in other embodiments, a single laser diode may be configured to output laser beams of a plurality of wavelengths.

The present disclosure may not be limited to the configurations and methods of the exemplary embodiments related to the measurement apparatus, but it may also be applicable to various measurements of other portions of a human body or commercial measurements of other objects, organisms, or beings. For example, the measurement apparatus disclosed herein may also be applied to the measurements of other lesions, such as those related to carpel tunnel syndrome, or the measurements of spoliation levels of plants. Also, a part or all of those exemplary embodiments may be combined to derive various variations.

What is claimed is:

1. A measurement apparatus comprising:
   a light source configured to output light toward a first side of an object;
   a sensor positioned relative to the light source to permit the object to be positioned between the light source and the sensor, wherein the sensor is configured to sense the light transmitted through the object; and
   an optical transmitter disposed at an upper portion of the sensor and comprising a plurality of optical fibers configured to transfer the transmitted light to the sensor,
   wherein:
   the light source comprises a laser diode configured to output a near-infrared laser beam;
   the optical transmitter comprises an upper optical fiber portion and a lower optical fiber portion;
   the upper optical fiber portion is positioned opposite the light source and the lower optical fiber portion is positioned between the upper optical fiber portion and the sensor; and
   the lower optical fiber portion is spaced apart from the sensor to define an empty gap between the lower optical fiber portion and the sensor, and the lower optical fiber portion is configured to transfer the transmitted light to the sensor,
   wherein the upper and lower optical fiber portions are is supported by a first structure of the measurement apparatus to be spaced apart from the sensor, wherein the sensor is supported by a second structure of the measurement apparatus to define the empty gap between the lower optical fiber portion and the sensor,
   wherein the optical transmitter comprises a top side configured to provide a surface on which the object is to be positioned and a bottom side adjacent to the sensor,
   wherein the light source comprises a mirror configured to reflect the near-infrared laser beam to be directed toward the sensor and is further configured to be tilted to change an angle of a reflective side of the mirror or moved along a path to change a position of the mirror,
   wherein the apparatus further comprises an optical direction adjuster comprising a plurality of optical fibers disposed between the mirror and the optical transmitter and configured to direct the near-infrared laser beam reflected from the mirror toward the object.

2. The apparatus of claim 1, wherein the plurality of optical fibers are divided into one or more portions wherein each portion is configured to transmit a corresponding portion of the transmitted light to the sensor.

3. The apparatus of claim 1, wherein the sensor is configured to convert the transmitted light to image data corresponding to an image.

4. The apparatus of claim 3, further comprising a controller configured to receive the image data and determine a condition of the object by comparing the received image data to stored image data.

5. The apparatus of claim 1, wherein the light source is movable to vary an output position of the light such that a measuring point of the object is changed.

6. The apparatus of claim 5, wherein the sensor is positioned relative to the light source to permit the object to be secured between the optical transmitter and the light source.

7. The apparatus of claim 5, wherein the light source comprises a plurality of light sources each separately controllable to output light.

8. The apparatus of claim 1, wherein the optical direction adjuster is further configured to direct the near-infrared laser beam reflected from the mirror toward the object in a direction perpendicular to the top side of the optical transmitter.

9. The apparatus of claim 1, further comprising an object information sensor configured to detect geometric information related to the object.

10. The apparatus of claim 9, wherein the object information sensor is configured to detect the geometric information using light output from the light source and reflected from the object.

11. The apparatus of claim 9, wherein the object information sensor comprises an object detector configured to measure at least a surface height or a shape of the object at a measurement position of the object.

12. The apparatus of claim 11, wherein the object detector includes a position displacement sensor or a 3D scanning sensor.

13. The apparatus of claim 1, wherein the light source is configured to output light of a predetermined intensity and wavelength.

14. The apparatus of claim 13, wherein the intensity of the output light is changed based on a determined characteristic of the object.

15. The apparatus of claim 14, wherein the characteristic of the object includes an optical characteristic or a geometric characteristic.

16. The apparatus of claim 1, wherein the gap defined between the lower optical fiber portion and the sensor is between 100 μm and 500 μm.

17. A measurement apparatus comprising:
   a light source configured to output light toward an object;
   an object information sensor configured to detect geometric information related to the object;
   a sensor configured to form a transmission image from the light output by the light source and transmitted through the object; and
   an optical transmitter disposed between a top surface of the sensor and the object and configured to transfer the transmitted light to the sensor,
   wherein:
   the light source comprises a laser diode configured to output a near-infrared laser beam;

the optical transmitter comprises an upper optical fiber portion and a lower optical fiber portion;

the upper optical fiber portion is positioned opposite the light source and the lower optical fiber portion is positioned between the upper optical fiber portion and the sensor;

the lower optical fiber portion is spaced apart from the sensor to define an empty gap between the lower optical fiber portion and the sensor, and the lower optical fiber portion is configured to transfer the transmitted light to the sensor, wherein the upper and lower optical fiber portions are is supported by a first structure of the measurement apparatus apart from the sensor supported by a second structure of the measurement apparatus to define the gap between the lower optical fiber portion and the sensor, wherein the optical transmitter comprises a top side configured to provide a surface on which the object is to be positioned and a bottom side adjacent to the sensor, wherein the light source comprises a mirror configured to reflect the near-infrared laser beam to be directed toward the sensor and is further configured to be tilted to change an angle of a reflective side of the mirror or moved along a path to change a position of the mirror, wherein the apparatus further comprises an optical direction adjuster comprising a plurality of optical fibers disposed between the mirror and the optical transmitter and configured to direct the near-infrared laser beam reflected from the mirror toward the object.

18. The apparatus of claim 17, wherein the optical transmitter comprises a plurality of optical fibers configured to transfer the transmitted light to the sensor by preventing distortion of the transmitted light.

19. The apparatus of claim 17, wherein the object information sensor is configured to detect the geometric information using the light output by the light source and reflected from the object.

20. The apparatus of claim 17, wherein the gap defined between the lower optical fiber portion and the sensor is between 100 μm and 500 μm.

21. The apparatus of claim 17, wherein the optical direction adjuster is further configured to direct the near-infrared laser beam reflected from the mirror toward the object in a direction perpendicular to a surface of the optical transmitter.

* * * * *